United States Patent [19]

Andersen

[11] 4,145,186
[45] Mar. 20, 1979

[54] STERILIZATION DETECTION DEVICE AND METHOD

[75] Inventor: Harold W. Andersen, Oyster Bay, N.Y.

[73] Assignee: H. W. Andersen Products Inc., Oyster Bay, N.Y.

[21] Appl. No.: 729,552

[22] Filed: Oct. 4, 1976

[51] Int. Cl.² .................... G01N 31/22; G01K 11/12
[52] U.S. Cl. .................... 23/232 R; 73/356; 422/57; 422/86
[58] Field of Search .......... 23/254 R, 232 R, 253 TP; 116/114 AM; 73/356

[56] References Cited

U.S. PATENT DOCUMENTS

| | | | |
|---|---|---|---|
| 2,998,306 | 8/1961 | Huyck et al. | 23/254 R |
| 3,098,751 | 7/1963 | Huyck et al. | 21/58 X |
| 3,112,999 | 12/1963 | Grosskopf | 23/254 R |
| 3,378,348 | 4/1968 | McConnaughey | 23/254 R |
| 3,507,623 | 4/1970 | McConnaughey | 23/254 R |
| 3,510,263 | 5/1970 | Hach | 23/253 TP |
| 3,620,677 | 11/1971 | Morison | 23/253 TP |
| 3,884,641 | 5/1975 | Kraffczyk et al. | 23/254 R X |
| 4,042,336 | 8/1977 | Larsson | 23/254 R X |

FOREIGN PATENT DOCUMENTS 1370470 10/1974 United Kingdom .................. 23/254 R

*Primary Examiner*—Joseph Scovronek
*Attorney, Agent, or Firm*—Frank J. Jordan

[57] ABSTRACT

In measuring the dose of sterilant delivered to an enclosed space, a mixture of a salt of a strong acid and a weak base and an acid-alkali indicator dye is disposed within a container element impermeable to the sterilant. The container has an opening, and the sterilant passes through the opening into the container where it reacts with successive moieties of the mixture to effect a color change relative to the unreacted mixture. The reaction progressively advances away from the opening as the dose of the sterilant increases, whereby the extent of the advancing color change indicates the integration of time, temperature and sterilant concentration delivered to the enclosed space.

16 Claims, 8 Drawing Figures

STERILIZATION DETECTION DEVICE AND METHOD

BACKGROUND OF THE INVENTION

This invention relates to a method and device for determining the dosage effected by a sterilant such as ethylene oxide to thereby determine that the required physical conditions within a sterilization chamber or the like have been effected. Sterilization by means of chemical sterilants is a combined function of the effects of concentration of the sterilant, temperature, and time of exposure to the sterilant.

Heretofore, "sterilization" indicator devices are known which indicate only exposure to sterilant. However, these known indicators are not capable of indicating the degree of sterilant dose effected at any particular time but rather only indicate a minimum exposure to sterilant. For example, U.S. Pat. No. 2,998,306 to Huyek et al relates to a telltale device purporting to indicate when sterilization has been completed, but without indicating the amount of sterilant dose effected at any particular intermediate period of time as in the case of applicant's invention. Moreover, the device in the aforementioned Huyek patent utilizes a film of material which is permeable to ethylene oxide, the film being of a predetermined thickness and composition so as to control the passage of ethylene oxide therethrough to the indicator enclosed within the permeable material. As previously mentioned, this known device undergoes a color change only after a predetermined minimal level of contact with ethylene oxide has been attained, that is when minimum sterilant exposure has been complete, and is not capable of indicating the amount of ethylene oxide contact at any particular period of time. Accordingly, the Huyek device can reliably be used only for one particular combination of variables under which sterilization is effected.

Accordingly, an object of the present invention is to overcome the disadvantages of such known devices and provide a sterilization indicating device which sustantially integrates the effects of time, temperature and sterilant concentration during the sterilization process.

Another object of the invention is to provide a relatively inexpensive sterilization indicating device which is adaptable for mass production.

Another object is to provide a sterilization indicating device which is easy to use, even by untrained personnel, which requires no moving parts, which is relatively small in size, and which is reliable in use.

Other features which are considered characteristic of the invention are set forth in the appended claims.

Although the invention is illustrated and described in relationship to specific embodiments, it is nevertheless not intended to be limited to the details shown, since various modifications and structural changes may be made therein without departing from the spirit of the invention and within the scope and range of equivalents of the claims.

The construction and operation of the invention, however, together with additional objects and advantages thereof will be best understood from the following description of specific embodiments when read in connection with accompanying drawings.

SUMMARY OF THE INVENTION

In measuring the dose of sterilant delivered to an enclosed space, a mixture of a salt of a strong acid and a weak base and an acid-alkali indicator dye is disposed within a container element impermeable to the sterilant. The container has an opening, and the sterilant passes through the opening into the container where it reacts with the sterilant with successive moieties of the mixture to effect a color change relative to the unreacted mixture. The reaction progressively advances away from the opening in proportion to the concentration of the sterilant, the time of exposure to the sterilant and the temperature whereby the extent of the advancing color change indicates the dose of sterilant delivered to the enclosed space.

DESCRIPTION OF THE PREFERRED EMBODIMENTS

Figure 1:
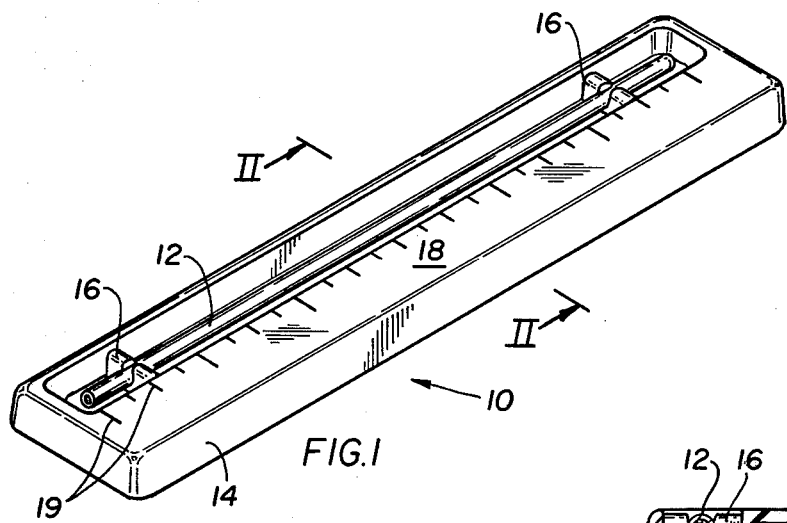
FIG. 1 is perspective view of one embodiment of the invention.
Figure 2:
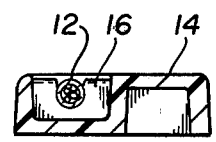
FIG. 2 is a cross-sectional view taken along line II—II in FIG. 1.

Referring to the drawings there is shown in FIG. 1 an indicator 10 which includes a tube 12 and a carrier 14. The carrier 14 includes holding means such as a pair of notched grips 16 although any convenient number of grips may be employed. As best seen in FIG. 2, the notch tapers inward and then opens to a circular region substantially equal in diameter to the tube 12 such that the tube 12 may be snapped in place and then held in a fixed position on the carrier 14.

Figure 3:
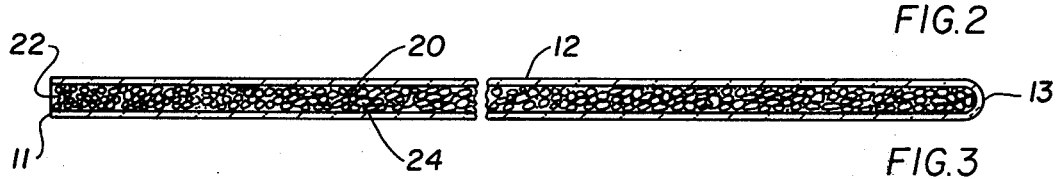
FIG. 3 is a cross-sectional view of the tubular member of the device of FIG. 1.

The tube 10 is filled with an inert carrier, one form of which might be of a particulate material 20 which may be a dry, fine sand and which may be coated with a mixture of a salt of a strong acid and a weak base, such as magnesium chloride, and an indicator dye, such as bromophenol blue or methyl red. The coated particulate material 20 is packed uniformly in the tube 12 through its open end 11. The other end of the tube 12 is sealed as indicated at 13 in FIG. 3. The coated particulate material 20 has a yellow color and when the tube 12 containing the yellow particulate material 20 is placed in an atmosphere containing a sterilant such as ethylene oxide, the magnesium chloride will react with the ethylene oxide to form magnesium hydroxide and ethylene chlorhydrin. The reaction is as follows:

$$MgCl_2 + 2H_2O + 2C_2H_4O + \text{(Bromophenol Blue)} \xrightarrow{\text{(yellow)}}$$
$$Mg(OH)_2 + 2C_2H_4ClOH + \text{(Bromophenol Blue)} \text{(blue)}$$

The structural formula is as follows:

$$Cl-Mg-Cl + 2\,h\underset{O}{\overset{O}{\diagup\!\!\!\diagdown}}h + 2H-\underset{O}{\overset{H}{\underset{|}{C}}\diagdown\!\!\!\diagup\overset{H}{\underset{|}{C}}}-H \longrightarrow$$

-continued

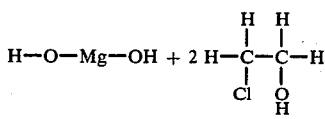

The reaction of the magnesium chloride with the ethylene oxide to form magnesium hydroxide and ethylene chlorhydrin causes a pH shift from the acid side of neutral to the alkaline side. Accordingly, the indicator coated particulate material 20 will change from yellow to blue. Since ethylene oxide is consumed in this reaction, albeit in tiny quantities at the point of reaction, the color change moves down the tube 12 with a sharp front. Accordingly, the length of the tube 12, its diameter, the acidity of the indicator coated particulate material 20, and the properties of the inert carrier can all be determined to achieve an indicator which changes color from end to end when enough ethylene oxide gas has been present for a sufficient length of time to react all the indicator. Properly calibrated, this integrates the effects of temperature, time and concentration of sterilant, and this can be related to the known parameters required for sterilization.

The mixture which is coated on the particulate material may contain an acid, for example citric, which serves as a control for regulating the speed of the reaction. For example, citric acid will serve to delay the color change reaction.

The chemical method for regulating the speed of reaction is as follows:

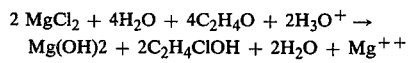

The acid reacts with the magnesium hydroxide produced by the reaction of ethylene oxide and magnesium chloride.

In addition to regulating the speed of the reaction by adding acid to the mixture as indicated hereinabove, additional magnesium chloride may be made available adsorbed on the inert carrier. Thus the more available magnesium chloride the slower the reaction will travel down the tube.

The acid salt such as magnesium chloride, the pH indicator such as bromophenol blue, and the acid such as citric acid are dissolved in water and the inert carrier is coated with this mixture by simply mixing together and drying at low heat and humidity. The coated silica is then placed in the tube 12 as previously described.

The ethylene oxide propelled by its own kinetic energy (a function of the temperature) enters into the open end 11 of the tube 12 and passes through the interstices between the coated silica particles. When the ethylene oxide molecule contacts a coated silica particle, the chemical reaction indicated above takes place raising the pH and changing the pH indicator from yellow to blue. As the open end portion of the tube becomes exhausted of magnesium chloride, the ethylene oxide must travel further and further down the tube 12, reacting with available magnesium chloride and changing the pH indicator from yellow to blue with a sharp front until the whole tube is exhausted of magnesium chloride and the blue color change extends down the full axial length of the tube 12.

The tube 12 may be made of glass or any material substantially impermeable to ethylene oxide. The carrier 14 may be made of plastic or the like.

In place of magnesium chloride, other salts of strong acids and weak bases may be used and many inert carriers other than silica may be used. This invention may be utilized with other gases or vapors, for example propylene oxide, vinyl chloride vapor, and the like.

Figure 4:
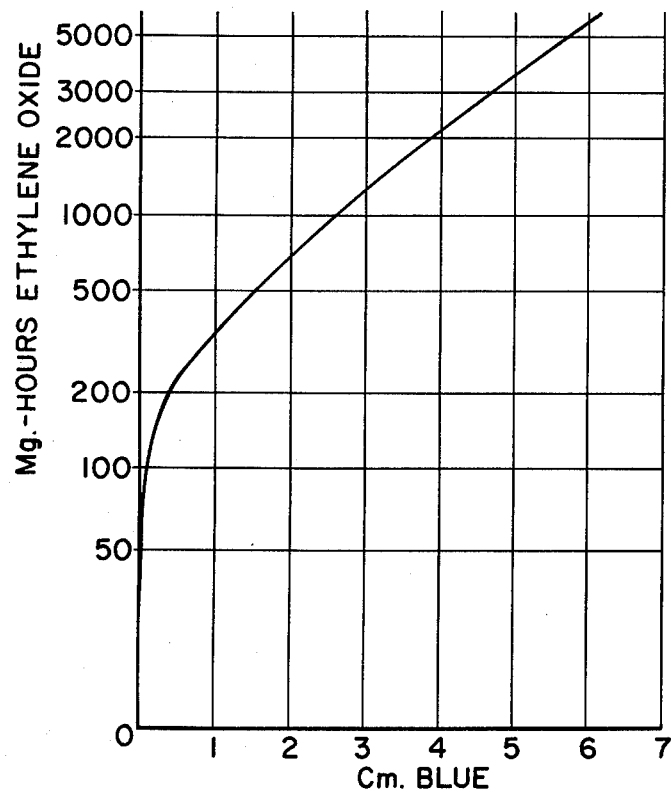
FIG. 4 is a graph in which milligram-hours ethylene oxide is plotted against centimeters of color change.

The surface 18 of the carrier 14 may be provided with indicia markings 19 corresponding to doses of ethylene oxide exposure for a particular or a variety of operating conditions. The calibration of the indicia markings 19 can be explained in connection with the graph of FIG. 4, wherein the dosage level in milligram hours of ethylene oxide is plotted against centimeters of blue indicator. Accordingly, the one centimeter point indicates 350 mg.-hr ETO, the two centimeter point 660 mg.-hr. ETO, the three centimeter point 1200 mg.-hr. ETO, the four centimeter point 2000 mg.-hr. ETO, the five centimeter point 3500 mg.-hr. ETO, and the six centimeter point 5500 mg.-hr. ETO. The operating temperature affects both the rate of color migration and the sterilization with increasing temperature producing corresponding increases in the rate of color migration and sterilization. For example, in one sterilization system operating at 20 degree Centigrade, 3000 mg-hours (ETO concentration in milligrams per liter times hours of exposure) is sufficient to provide satisfactory sterilization. On the other hand, in a heated system operating at 50 degrees Centigrade, 1500 mg-hours of exposure may be sufficient.

Figure 5:
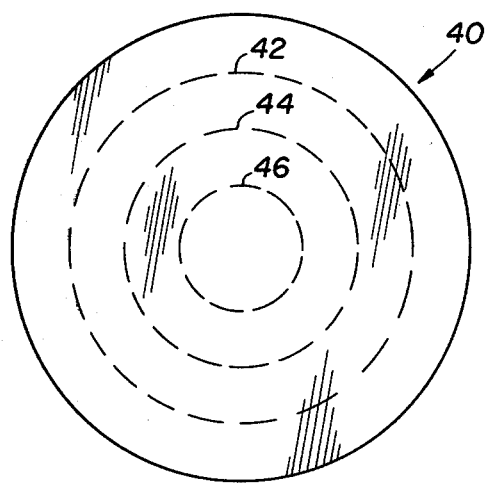
FIG. 5 is a plan view of a modified form of the invention.
Figure 6:
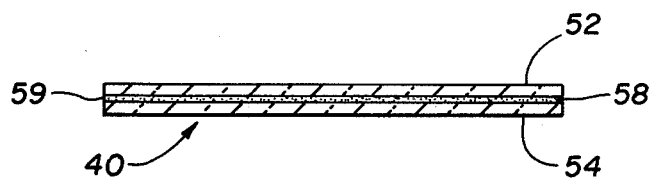
FIG. 6 is a cross-sectional view of the device shown in FIG. 5.

In the alternate embodiment of FIGS. 5 and 6, the indicator is in the form of a disc 40 and the color change system is sandwiched between a pair of disc elements 52, 54, which may be impermeable films. Polyester and polyamide films are examples of the types of films which may be used. The film discs 52, 54 are preferably self-adhesive mylar strips. At least one of the discs is translucent or transparent. In one form of this modification, the inert carrier is a quick drying ink 58 placed between the film discs 52, 54. The ink may be produced by mixing the salt of a strong acid and a weak base, for example magnesium chloride, with a pH indicator, for example bromophenol blue, which changes color of about pH 4, talc, and clear printers varnish to produce a relatively quick drying yellow ink.

The ink 58 is printed on one of the discs for example disc 54 and after it dries, the other disc 52 is laminated to the upper surface of the ink 58 to thereby provide a layer of ink 58 securely sandwiched between the two layers of ethylene oxide impermeable film layers 52, 54. The ethylene oxide enters along the entire peripheral edge 59 and gradually passes radially inwardly. As the exposure dosage increases, the ink 58 which is yellow in the example indicated changes color from yellow to blue. As the exposure continues to increase and the ethylene travels further radially inwardly, the yellow circle becomes smaller and smaller and the blue perimeter becomes larger, creating a "bull's eye" effect.

The transparent surface can be overprinted to mask the color change thus providing different graphic presentations.

The disc configuration can be calibrated in milligram-hours of ethylene oxide exposure in a manner similar to that of the tubular indicator of FIG. 1. Accordingly, the rings 42, 44 and 46 in FIG. 5 represent progressively increasing dosages. The indicator can be calibrated so that the blue perimeter reaches a particular ring 42, 44 and 46 to indicate a particular dosage or such that the yellow circle disappears and is totally replaced with blue when the necessary ethylene oxide dose was present to effect the required sterilization.

An inert carrier might consist of a chemically treated porous filter paper. Thus referring to FIG. 6, the chemically treated porous filter paper would replace the ink 58. The filter paper may include a mixture of a strong acid and a weak base for example magnesium chloride with a pH indicator, for example bromophenol blue, which changes color at about pH 4. The operation of the device using the porous filter paper is essentially the same as that previously described in connection with utilization of the ink and accordingly, a detailed description of the operation is not deemed necessary.

Instead of using a round disc, the previously described unit, may be employed in elongated form. For example, in a modification shown in FIGS. 7 and 8, the indicator is in the form of an elongated strip and the color change material 66 is sandwiched between a pair of elongated strips 62, 64 which are ethylene oxide impermeable films as previously described in connection with the embodiment of FIGS. 5 and 6. The indicating material 66 may be in the form of a quick drying ink or a chemically treated porous filter paper as previously described. At least a portion of at least one strip is translucent or transparent to permit viewing of the color change material 66.

In this embodiment, the peripheral edges around the indicating material 66 are sealed, except for the end 68 which is open. Thus, the two strips 62, 64 are sealed to one another at both longitudinal edges 70 and 72 and also at one end 74. Accordingly, ethylene oxide can only enter into the indicator through the open end 68 and thus passes through the ink or chemically treated porous filter paper progressively, reacting with the available magnesium chloride and changing the pH indicator from yellow to blue with a sharp front.

Figure 7:
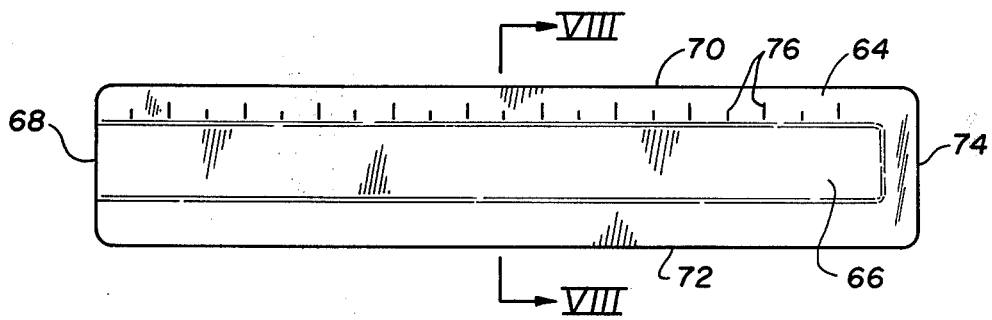
FIG. 7 is a plan view of another modified form of the invention.
Figure 8:
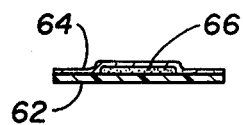
FIG. 8 is a cross-sectional view taken along the line VIII—VIII in FIG. 7.

The strip may be calibrated as indicated at 76 to indicate the degree of sterilization effected as indicated by the demarkation between the yellow and blue color. It will be seen that the operation of the embodiments of FIGS. 7 and 8 is similar to the operation of the main embodiment shown in FIGS. 1 to 3 in that the integrated exposure to sterilant is indicated on an elongated member.

The above described devices are used by placing them in, a gas sterilizer containing articles to be sterilized, and the ethylene oxide sterilizing gas is fed to the space or chamber.

The device of the present invention may have suitable calibrations thereon to indicate the dose of ethylene oxide to which it has been exposed. In some cases, more than one scale may be provided depending on the temperature at which the device is used. For example, one scale might be provided to indicate that complete sterilization has been effected at 3000 mg-hours, this latter being utilized, for example, when operating at 20 degree Centigrade. Also a second scale or indication may be provided on the same device to indicate that complete sterilization has been effected at 1500 mg-hours, for example, when operating at a temperature of 50 degrees Centigrade.

It will be observed that because of the sharp front between the color change and the progressive movement of the front along the indicator, it is possible to determine the integration of time, temperature and sterilant concentration effected at any particular moment. Accordingly, it is possible for an observer or operator to look at the indicator and determine, for example, that sterilization conditions have only been one-quarter or one-half attained by reading the appropriate scale adjacent the color line between the yellow and blue. This provides an advantage to an operator as he can determine how much or to what degree the "sterilization has been completed" and how much additional exposure to sterilant is required.

It can be seen from the foregoing description that the sterilant is prevented from coming into simultaneous contact with the entire quantity of magnesium chloride through the use of a sterilant gas barrier. The sterilizing gas must traverse the initially contacted magnesium chloride and continually contact and traverse successive moieties of magnesium chloride until all of the magnesium chloride is converted to magnesium hydroxide. It is thus seen that a time factor is built into the reaction between the ethylene oxide and the magnesium chloride. The presence of an acid, such as citric acid, serves to react with the formed magnesium hydroxide and maintain the pH on the acid side so as to retard the color shift from yellow to blue (in the case where bromophenol blue is used). Increasing the magnesium chloride concentration slows down the rate of travel of unreacted ethylene oxide through the indicator. A balance is established between the acid concentration and the magnesium chloride concentration, so that substantially all of the magnesium chloride must be converted to the hydroxide before a color change occurs.

It is thought that the invention and many of its attendant advantages will be understood from the foregoing description and that it will be apparent that various changes may be made in the form, construction, and arrangements of the parts without departing from the spirit and scope of the invention or sacrificing all of its material advantages. The form heretofore described being merely one preferred embodiment thereof.

What is claimed is:

1. A method of measuring the instantaneous degree of effectiveness of a sterilant delivered to an enclosed space comprising the steps of coating a mixture of a salt of a strong acid and a weak base and an acid-alkali indicator dye on particles of an inert carrier, disposing said coated carrier particles within a container element such that interstices are provided between the coated carrier particles, said container element being impermeable to said sterilant, said container having an opening, passing said sterilant directly from said enclosed space through said opening into said container, reacting said sterilant with said mixture to effect a color change relative to the unreacted mixture, advancing said sterilant through the interstices between said coated particles such that the salt in the mixture on the coated particles closer to said opening is exhausted by the sterilant to effect a color change before said sterilant advances to the next adjacent particles further removed from said container opening, said color change between said reacted and unreacted mixture being defined by a discernible line of demarkation, and progressively advancing said line of demarkation away from said opening as the time, temperature and concentration of said sterilant in said enclosed space increases, calibrating said container element by providing calibrated indicia fixedly positioned relative to said container element to provide various and successively progressive indications of the effectiveness of said sterilant, and measuring the instantaneous degree of effectiveness of said sterilant delivered to said enclosed space by the position of said line of demarkation relative to the calibrated indicia.

2. A method according to claim 1 wherein said carrier is a form of silica known commercially as "sand."

3. A method according to claim 1 wherein said mixture is in the form of an ink which further comprises talc and printers varnish.

4. A method according to claim 1 further comprising controlling the speed of reaction of said sterilant with said mixture by varying the amount of available salt.

5. A method according to claim 1 wherein said sterilant is ethylene oxide.

6. A method according to claim 1 wherein said sterilant is propylene oxide.

7. A device for measuring the instantaneous degree of effectiveness of a sterilant delivered to an enclosed space comprising a container element impermeable to said sterilant, a mixture of a salt of a strong acid and a weak base and an acid-alkali indicator dye coated on particles of an inert carrier, said coated particles being disposed with the container element such that interstices are provided between the coated particles within said container element, means on said container element defining an opening leading directly to said enclosed space, said sterilant entering said container element directly through said opening and reacting with said mixture to effect a color change relative to the unreacted mixture, said interstices between said coated particles defining passageways for said sterilant to pass and thereby providing for the sterilant to advance along the container element whereby the salt in the mixture on the coated particles closer to said opening is exhausted by the sterilant to effect a color change before said sterilant advances through said interstices to the next adjacent particles further removed from said container opening, said color change between said reacted and unreacted mixture being defined by a discernible line of demarkation, means defining calibrated indicia fixedly positioned relative to said container element to provide indications of the position of said line of demarkation, said line of demarkation progressively advancing away from said opening as the time, temperature and concentration of said sterilant increases, whereby the instantaneous degree of effectiveness of said sterilant delivered to said enclosed space is indicated by the position of said line of demarkation relative to said calibrated indicia.

8. A device according to claim 7 wherein said container element is an elongated glass tube open at one longitudinal end thereof.

9. A device according to claim 7 further comprising a holder means for holding said container element.

10. A device according to claim 9 wherein said container element is detachably mounted on said holder means.

11. A device according to claim 7 wherein said container element is in the form of two spaced discs, said coated particles being disposed between said spaced discs, said opening means being disposed about the periphery of said discs.

12. A device according to claim 11 wherein said discs are made from a material selected from the group consisting of polyester and polyamide films.

13. A device according to claim 11 wherein at least a portion of one of said films is translucent or transparent to permit viewing of said mixture.

14. A device according to claim 7 wherein said container element is in the form of two elongated strip means, said coated particles being disposed along an elongated portion between said strip means, said opening means being disposed at one logitudinal end of said strip means.

15. A device according to claim 7, wherein said calibrated indicia means is provided on a holder means which holds said container element.

16. A device according to claim 7, wherein said calibrated indicia means is provided on said container element.

* * * * *